(12) United States Patent
Andersson et al.

(10) Patent No.: US 7,537,925 B2
(45) Date of Patent: May 26, 2009

(54) **MUTATED *LACTOCOCCUS* STRAIN**

(75) Inventors: Ulrika Andersson, Veberöd (SE); Peter Rådström, Bjärred (SE)

(73) Assignee: Forskarptent I SYD AB, Lund (SE)

( * ) Notice: Subject to any disclaimer, the term of this patent is extended or adjusted under 35 U.S.C. 154(b) by 56 days.

(21) Appl. No.: 11/336,523

(22) Filed: Jan. 20, 2006

(65) Prior Publication Data
US 2006/0270011 A1 Nov. 30, 2006

Related U.S. Application Data

(63) Continuation of application No. 10/814,674, filed on Mar. 30, 2004, which is a continuation of application No. PCT/SE02/01805, filed on Oct. 3, 2002.

(51) Int. Cl.
*C12N 1/20* (2006.01)
*C12P 1/00* (2006.01)
*A01N 63/00* (2006.01)

(52) U.S. Cl. .................. 435/252.9; 435/252.1; 435/243; 435/41; 435/170; 424/93.45; 424/93.4; 424/93.1

(58) Field of Classification Search ........................ None
See application file for complete search history.

(56) References Cited

FOREIGN PATENT DOCUMENTS

WO   WO/97/13842   4/1997

OTHER PUBLICATIONS

"The influence of limiting and non-limiting growth conditions on glucose and maltose metabolism in *Lactococus lactis* ssp. *lactis* strains"; Sjoberg et al.,; Department of Applied Microbiology; Lund Institute of Technology/University of Lund; 1995; pp. 931-938.

"Insertional mutagenesis in *Lactococcus lactis* subsp. *lactis* mediated by IS946"; Dinsmore et al.,; FEMS Microbiology Letters; 1993; Federation of European Microbiological Societies; pp. 43-48.

"Isolation of chromosomal mutations of *Lactococcus lactis* subsp. *lactis* biovar. *diacetylactis* 18-16 after introduction of Tn919"; FEM Microbiology Letters; 1991 Federation of European Microbiological Societies; pp. 135-140.

"A System To Generate Chromosomal Mutations in *Lactococcus lactis* Which Allows Fast Analysis of Targeted Genes"; Law et al., Journal of Bacteriology; Department of Genetics, University of Groningen, Netherlands; 995; vol. 177, No. 24; pp. 7011-7018.

"Physiological Role of β-Phosphoglucomutase in *Lactococus lactis*"; Levander et al., Applied and Environmental Microbiology; Oct. 2001; p. 4546-4553 vol. 67, No. 10; Lund Institute of Technology, Lund University, Lund, Sweden.

"Metabolic engineering of lactic acid bacteria: overview of the approaches and results of pathway rerouting involved in food fermentations"; Hugenholtz et al., Current Opinion in Biotechnology, 1999; pp. 492-497.

"Genetic localization and regulation of the maltose phosphorylase gene, *malP*, in *Lactococcus lactis*", Nilsson et al., Applied Microbiology; 2001; Lund University, Lund Sweden; pp. 1565-1573.

*Primary Examiner*—Lora E Barnhart
(74) *Attorney, Agent, or Firm*—Gauthier & Connors LLP

(57) ABSTRACT

A mutant of *Lactococcus lactis* spp. *lactis*, which produces lactate at high volumetric and specific productivity as well as high amounts of lactate dehydrogenase, as well as the use of said strain, and a method for producing lactate, as well as the use of the lactate thus produced.

10 Claims, 2 Drawing Sheets

MUTATED *LACTOCOCCUS* STRAIN

PRIORITY INFORMATION

This application is a continuation of U.S. patent application Ser. No. 10/814,674 which was filed on Mar. 30, 2004 which is a continuation of Int'l Patent Application No. PCT/SE02/01805, filed on Oct. 3, 2002, and which claims priority to Swedish Patent Application No. 0103294-4, filed on Oct. 3, 2001, all of which are incorporated herein in their entirety.

DESCRIPTION

1. Technical Field

The present invention relates to a new lactate producing strain belonging to the *Lactococcus* genus, viz. a mutant of *Lactococcus lactis* spp. *lactis* 19435 (obtained from American Type Culture Collection (ATCC), 10801 University Boulevard, Manassas, Va. 20110-2209), as well as a use of the mutant for lactate production, and a method for producing lactate.

2. Background of the Invention

Lactic acid is a naturally occurring organic acid that can be produced by either chemical synthesis or carbohydrate fermentation. Both of these production routes are used commercially [Datta, (1995)]. Chemical synthesis results in racemic lactic acid, while fermentation technologies enable synthesis of a desired stereoisomer of lactic acid. In the literature there are several reports concerning metabolic engineering of lactic acid bacteria in order to assess and enhance their ability in lactic acid production from different carbohydrates. Existing commercial production processes use homolactic organisms such as *Lactobacillus delbrueckii* and *Lb. bulgaricus* [Datta, (1995)].

*Lactococcus lactis* is one of the most studied organisms used for industrial applications. *L. lactis* ferments glucose according to a homolactic pathway under non-limiting glucose conditions [Sjöberg, (1995)]. This organism primarily produce the L-isomer of lactic acid that is favoured in applications associated with food since the D-isomer is harmful to humans [Hofvendahl, (1997)]. The post-glycolytic pyruvate metabolic pathways play a key role in determining the outcome of a fermentation of *L. lactis*. Activities of pyruvate converting enzymes changes with different cultivation conditions which lead to the important variations of end product formation [Cocaign-Bousquet, (1996)] (and references therein). In this study we describe a mutant of *Lactococcus lactis* ssp. *lactis* that is able to produce lactate twice as fast as the wild type strain under non-limiting glucose conditions. Our report concerns a physiological and biochemical characterisation of the mutant lactococcal strain in order to assess differences in glucose uptake and activities of important enzymes involved in glycolysis and pyruvate conversion compared to the wild type strain.

Lactic acid is a chemical used in food technology as well as in general chemical industry, including polymer technology. Thus, it can be used to produce polymers or become hydrogenated to produce propylene glycol, and other carbon chemical intermediates. Lactic acid is of interest to produce biocompatible and decomposable polymers, polylactic acid (PLA), used to produce sutures or implants, i.e., to be used within medicinal and veterinary surgery.

50,000 tonnes of lactate are produced each year around the world, which indicates that it is a relatively attractive product. Two thirds are recovered from fermentation processes while one third is derived from a synthetic production from mostly lacto-nitrile. The drawback of using a synthetic production is that the lactate recovered is a racemate, i.e., containing equal amounts of L- and D-isomers in a mixture. The drawback of having a racemate is that it is considerably harder to polymerise the lactate at such an application. Pure D- or L-lactate polymers are crystalline and stable, while polymers of mixtures are amorphous.

Lactic acid is an expensive chemical when produced by fermentation of different lactic acid producing micro-organisms, as the fermentation produces lactate, i.e., a salt of lactic acid, which has to be recovered from the fermentation broth also containing proteins and lactic acid producing cells. In order to produce a more cost beneficial lactic acid and/or lactate, the fermentation has to utilise a micro-organism which produces a high concentration of lactate defined as overall concentration, but also defined as specific productivity ($Q_s$), i.e., grams per gram of substrate, and volumetric productivity ($Q_v$), i.e., grams per liter of broth per hour.

Lactic acid is present in two enantiomeric forms, L-lactic acid, and D-lactic acid. As D-lactic acid is toxic to humans, and should not be present in food applications, there is a demand for increased production of L-lactic acid. Lactic acid is produced during fermentation by means of an enzyme, lactate dehydrogenase, LDH. LDH is present in two forms, L-LDH for production of L-lactate, and D-LDH for the production of D-lactate. The lactococci will thus also produce and activate a D-LDH, i.e., a lactate dehydrogenase producing the D-isomer.

U.S. Pat. No. 4,885,247 relates to a method for recovery and purification of lactate salts from whole fermentation broth using electrodialysis, whereby the method is stated to efficiently recover the lactate as a concentrated liquid. The lactate recovered is then transformed into lactic acid.

Sjöberg, A., Persson, I., Quednau, M., and Hahn-Hägerdahl, B., in Applied Microbiology and Biotechnology 42(6): 931-938, (1995) discuss the influence of limiting and non-limiting carbohydrate conditions of glucose and maltose metabolism in *Lactococcus lactis* spp. *lactis* strains. In this paper three different lactococci strains are shown with regard to their lactate production at growth under carbohydrate limiting and non-limiting conditions. The carbohydrates studied are maltose and glucose. One mutant, AS211 was formed from 19435 after a novobiocin-treatment. AS211 has a 20% higher production of lactate compared with the 19435 strain at continuous fermentation of glucose. AS211 was grown at $D=0.6\ h^{-1}$.

STN database, CAPLUS, acc. no. 1992:549358, L-lactate production from xylose employing *Lactococcus lactis* IO-1, Biotechnology Letters, 14(7):599-604, (1992), and Dialog database, acc. no. 0137847, L-lactate production from xylose employing *Lactococcus lactis* IO-1-effect of inoculum C-source, xylose concentration, product inhibition and, mixed substrate on L-lactic acid production, Biotechnology Letters, 14(7):599-604, (1992) by Ishizaki, A. et al relates to work on *Lactococcus lactis* IO-1 with regard to different parameters which may influence the L-lactate production from a mixture of glucose and xylose. The basis for the study was to investigate whether L-lactate production may be optimised using a cheap raw material such as lignocellulose hydrolysate. Lignocellulose hydrolysate contains both xylose and glucose, which are used for the conversion into L-lactate. Using a mixture of glucose and xylose the production of L-lactate is 0.67 grams of lactate per gram of sugar. There is no indication in the paper of which subspecie (spp) *L. lactis* IO-1 belongs to.

Dialog database, acc. no. 07450183, General character and taxonomic studies of *Lactococcus lactis* IO-1 JCM 7638, Jour. of the faculty of agriculture, Kyushu University, 35(1-

2):1-8, (1990) by Ishazaki, A., et al, relates to the characterisation of the strain *L. lactis* IO-1, i.e., the strain discussed above. There is no indication in the paper of which subspecie (spp) *L. lactis* IO-1 belongs to.

Dialog database, acc. no. 00324956, Fermentative production of L-lactate from xylose, Conference paper, Developments in food engineering: Proceedings of the 6th International Congress on Engineered Food, Chiba, 2(4):552-554, (1993), by Ueda, T., et al, relates to *L. lactis* IO-1. Its ability of producing L-lactate from xylose is discussed.

STN database, CAPLUS, acc. no. 1994:571806, Cloning, sequencing, and comparison of three lactococcal L-lactate dehydrogenase genes, Microbiology 140(6):1301-1305, (1994), by Swindell, S. R., et al compares DNA sequences of genes coding for the enzyme L-lactate dehydrogenase (LDH) of different *Lactococcus* strains. It proves that the DNA sequences are strongly conserved between the different strains.

STN database, acc. no. 0167424, Stimulation of the rate of L-lactate fermentation using *Lactococcus lactis* IO-1 by periodic electrodialysis L-lactic acid and production, Jour. of Fermentation and Bioengineering, 77(5):508-512, (1994), by Vonktaveesuk, P., et al, discloses electrodialysis of the products obtained by fermentations with strain *L. lactis* IO-1.

STN database, acc. no. 1991:523825, Differences between *Lactobacillus casei* spp casei 2206, and citrate-positive *Lactococcus lactis* spp. *lactis* 3022 in the characteristics of diacetyl production, Applied and Environmental Microbiology, 57(10):3040-3042, (1991), by Kaneko, T., et al compares a lactococci, *Lactococcus lactis* spp. *lactis* and a lactobacilli, *Lactobacillus casei* spp. *casei* with regard to the production of diacetyl. In reality the LDH productions of the two strains are compared whereby the lactobacilli strain has 3 times higher production of LDH than the lactococci strain. The basic medium used is not disclosed.

SUMMARY OF THE PRESENT INVENTION

It has now been developed a new mutant of the wild type strain *L. lactis* spp. *lactis* 19435, which mutant strain, under given conditions produces high concentrations, expressed both as $Q_s$ and $Q_v$ of L-lactate. Said mutant activates D-LDH, and L-LDH at different optima which provides for a differentiated production of D- and L-lactic acids.

The mutant can be used for high yield production of lactate to be used in food technology or as a commodity in chemical industry in general.

DETAILED DESCRIPTION OF THE INVENTION

The present invention is based upon a mutant of *Lactococcus lactis* spp. *lactis* wild type strain 19435 (obtained from ATCC), which mutant has been deposited on the 4 of Sep., 2001 at Deutsche Sammlung von Mikroorganismen und Zellkulturen under deposition number DSM 14489 in accordance with the Budapest Treaty.

It is at present unknown where in the genetic code the mutation has occurred and to what extent the mutation has changed the genetic code.

At controlled, monitored fermentations (continuous fermentations) of the new mutant, herein called TMB5003, the lactate production has been analysed and calculations made show that TMB5003 has double the volumetric production compared to the wildtype strain 19435, and has a specific productivity which is 1.5 times that of the wildtype strain. The yield of lactate calculated as grams of lactate produced per gram of glucose added at the fermentation, was calculated to be the same for both strains at continuous fermentations.

The different tests made on the new mutant TMB5003 show, as will be evident from below that the new mutant has an unrestricted uptake of glucose which is transformed into lactate via a doubled metabolic capacity.

It has turned out that L-LDH, and D-LDH are produced or activated at different growth conditions, and thus the conditions can be chosen to produce optimal amounts of the lactate preferred, in this case the L-lactic acid or L-lactate.

Bacterial Strains and Cultivation Conditions

*Escherichia coli* DH5α (Life Technologies Inc.) was grown in Luria-Bertani medium at 37° C. and erythromycin was added to a concentration of 250 μg ml$^{-1}$ when required. For standing batch cultures, *L. lactis* strains were cultivated at 30° C. in M17 medium (Oxoid) containing 10 g l$^{-1}$ sugar. For all lactococcal cultivations, sugars were autoclaved and added separately to the cultures as well as erythromycin was added to a final concentration of 2 μg ml$^{-1}$ when required to select for TMB5003. In experiments using pH-controlled batch cultivations, the lactococcal strains were grown in a medium of the following composition (per liter): tryptone (Merck), 5 g; yeast extract (Merck), 5 g; casamino acids (Difco Laboratories), 1 g; $K_2HPO_4$, 2.5 g; $KH_2PO_4$, 2.5 g and $MgSO_4.7H_2O$, 0.5 g, (pH 6.8). Carbohydrates were added to a final concentration of 10 g l$^{-1}$ respectively. The pH-controlled batch fermentations were performed at 30° C. in fermenters with a working volume of 800 ml. Stirring was set to 250 r.p.m. and the pH to 6.5, which was controlled by automatic base (3.0 M KOH) addition. The controlling device was a laboratory pH meter (Radiometer, Copenhagen, Denmark). The parent cultures were grown overnight in the same media as the respective experimental cultures, in standing batch cultures at 30° C. The inoculum 5% (vol/vol) was centrifuged, washed twice and resuspended in fresh culture medium without sugar, before being added to the experimental cultures.

For physiological characterisation and comparison of *L. lactis* spp. *lactis* ATCC19435 and *L. lactis* spp. *lactis* TMB5003, these strains were cultivated in semi-defined medium (SD3) according to van Niel and Hahn-Hagerdahl, (1999). All components except for potassium phosphates and water, were sterile filtered. Glucose was autoclaved and added separately to the medium at a final concentration of 5 g l$^{-1}$. Continuous cultivations were performed using chemostat conditions in Biostat® A fermenters (B. Braun Biotech International, Germany). The volume in the fermenters was kept at 1 l. The temperature was set at 30° C. and the pH was maintained at 6.5 using automatic base (10 M KOH) addition by the use of an automatic controlling device, micro-DCU system (B. Braun Biotech International, Germany). The stirring was kept at 150 r.p.m. using a MCU-200 system (B. Braun Biotech International, Germany). Anaerobic conditions were withheld by continuous nitrogen flushing through the medium at 0.2 ml min$^{-1}$. Precultures for fermentations were grown overnight in M17 medium containing 10 g l$^{-1}$ glucose. Precultures were harvested by centrifugation at 5000×g, 2° C. for 10 min, washed twice and resuspended in sterile double distilled water and finally inoculated at 2.5% (vol/vol) into SD3 medium containing 5 g l$^{-1}$ glucose. Continuous cultivations were started when the glucose was depleted from the batch cultures. Continuous fermentations were run in duplicates at each dilution rate for both lactococcal strains.

Measurement of Growth, Substrate Consumption and Product Formation

Measuring the optical density (OD) at 620 nm, using appropriate dilutions, on a Hitachi U-2000 spectrophotometer (Hitachi Ltd., Tokyo, Japan), monitored cell growth. Dry weight was measured for all cultures. Samples for substrate and product determination were filtered immediately through 0.2 μm filters after sampling and kept at −20° C. until analysis. Glucose, lactate, formate, acetate and ethanol were separated at 45° C. on an ionexchange column (Aminex HPX-87H, BioRad) and quantified using a refractive index detector (Shimadzu, Japan). The mobile phase was 5 mM $H_2SO_4$ at a flow rate of 0.6 ml $min^{-1}$.

Cell Extract Preparation, Protein Determination and Enzyme Assays

Lactococcal cells were withdrawn from the cultivations at appropriate times and harvested by centrifugation at 5000×g, 2° C. for 10 min. The cells were washed twice and resuspended in 20 mM triethanolamine buffer, pH 7.2, containing 0.5 mM EDTA and 0.5 mM dithiotreitol. Disintegration of cells was performed by vortexing (3×5 min) at 8° C. by the use of glass beads (0.5 mm, KEBO). Cell debris was removed by centrifugation at 19,500×g, 2° C., for 15 min. Cell extracts were kept at −80° C. until used. The protein concentration was determined according to the method of Bradford [Bradford, (1976)]. Bovine serum albumin was used as a standard.

All chemicals used in the enzyme assays were obtained from Sigma-Aldrich. LDH and PK activity was measured in the direction of NADH oxidation at 340 nm according to Hillier and Jaga, (1982), and Crow and Pritchard, (1982), respectively. The activity of PFK and GAPDH was determined according to the methods of Plaxton and Storey, (1986) and Brooks and Storey, (1988), respectively.

Glucose Transport Measurement

The uptake of glucose by lactococcal cells was measured according to the zero-trans-influx assay adapted for bacterial cells. Cells were collected at appropriate times and harvested by centrifugation at 5000×g, 2° C., for 10 min. Cell pellets were washed twice in ice-cold 0.1 M potassium phosphate buffer, pH 6.5, and finally resuspended to a dry weight of 25-30 mg $ml^{-1}$ using the same buffer. Cells were kept on ice until used. In the assay 20 μl of 0.1 M potassium phosphate buffer, pH 6.5, and 20 μl of cell resuspension were added to a plastic 5 ml reaction vial (Sarstedt) and incubated at 30° C. for 5 min. Ten microlitres of $^{14}C$-labelled glucose (Amersham Life Science) of concentrations between 0.3125 mM to 200 mM was added to the mixture to a final specific activity of 200 counts per minute (cpm) per nmol, and the assay was started by vortexing the vial shortly. The assay was allowed to proceed for 10 seconds, measured by the use of a metronome, and stopped by adding 3 ml of ice cold 0.5 M glucose from a dispenser. The reaction mixture was rapidly filtered through a glass micro-fibre filter (GF/F, 25 mm, Merck Eurolab). The reaction vial was washed twice with 3 ml ice-cold 0.5 M glucose solution and finally the filter equipment was also washed twice with ice-cold 0.5 M glucose solution. The filter was placed in a scintillation vial containing 5 ml scintillation solution (Ecoscint™ A, Hinzte AB, Sweden). Assays were run in duplicates and for every cell resuspension and for every glucose concentration a background sample was prepared. These samples were prepared and handled as the other tests but the assay was not started by vortexing, instead 3 ml ice-cold 0.5 M glucose solution was dispensed into the vial and the reaction mixture was filtered immediately.

Genetic Techniques and Development of L. lactis TMB5003

All DNA-modifying enzymes were obtained from Roche Diagnostics Scandinavia AB, Sweden. Plasmid preparations were performed using a Bio-Rad Quantum prep kit (Bio-Rad) and chromosomal DNA was prepared using an Easy-DNA™ kit (Invitrogen). Polymerase chain reaction (PCR) was performed using PwoII polymerase according to manufacturer's description. DNA fragments were purified from agarose gel using a Qiaquick kit (Qiagen). Restriction enzyme digestions and ligations were performed according to standard procedures [Sambrook, (1989)]. Ultra-competent E. coli cells were prepared and transformed as previously described [Inoue, (1990)]. Preparation and transformation of lactococcal cells were performed according to a protocol by Holo and Nes, (1989).

A 850 bp internal fragment of the L. lactis maltose phosphorylase encoding gene, malP, [Nilsson, Microbiology, 147: 1565-1573, (2001)] was amplified by PCR using primers 5'-ggcggatcctaaaggatttactgg-3' (forward), containing a BamHI restriction enzyme recognition site and 5'-ggcctgcag-caacttcttcgcttg-3'(reverse) containing a PstI restriction recognition site and L. lactis ssp. lactis 19435 chromosomal DNA as template. The PCR product was cleaved with restriction enzymes BamHI and RsaI, resulting in a 450 bp product. A minimal integration vector, pFL20, not able to replicate in lactococci, developed by Levander et al., (2001), was digested with suitable restriction enzymes and ligated with the 450 bp malP internal fragment. The resulting construct, denoted pTMB5003, was propagated in E. coli and further transformed into L. lactis spp. lactis 19435. Four transformants were obtained on erythromycin selective plates due to a single cross-over event in the malP of L. lactis. All transformants appeared to have the same growth behaviour in glucose and maltose cultivations, respectively. One transformant, called L. lactis spp. lactis TMB5003, was chosen for further investigations.

The new mutant has been tested during glucose fermentation runs, and thereby been compared with the type strain.

Growth and Product Formation

L. lactis spp. lactis 19435 and L. lactis spp. lactis TMB5003 were grown in pH-controlled batch cultures to assess and compare their growth behaviour on glucose (FIG. 2). The maximum specific growth rate of TMB5003 was twice the one that was determined for wild-type lactococci under the same growth conditions. When measuring the consumption of glucose during the cultivations it was obvious that TMB5003 consumed glucose approximately twice as fast as the wild type. Batch cultivations using lactose or maltose as sole carbon source resulted in no growth for TMB5003 in any of the cultivations while 19435 grew with the same specific growth rate on lactose as in glucose cultivations and with a slightly lower rate on maltose (data not shown). The inability of TMB5003 to ferment lactose was confirmed by investigating the plasmid content of these cells. TMB5003 had lost one plasmid, compared to wild-type lactococci, most likely to be the one harbouring the lac-operon (data not shown) [de Vos, (1990); de Vos, (1989); Maeda, (1986)]. The inability of the mutant strain to ferment maltose was due to the fact that the maltose operon was disrupted by insertion of pTMB5003 in the maltose phosphorylase encoding gene, malP (Nilsson and Radstrom, (2001)). It is believed that the alteration in the maltose operon does not promote the effect on glucose metabolism in TMB5003 and therefore this is not further discussed in the current presentation.

Product formation was investigated when lactococcal cells were cultivated continuously using glucose as sole carbon source under limiting and non-limiting conditions. TMB5003 was shown to produce lactate by a volumetric productivity twice as high as that for 19435 under glucose non-limiting conditions (Table 1). However, when glucose was limiting, the lactate productivity decreased markedly for TMB5003, beyond the values of wild-type lactococci. These results suggest that the mutant strain has a stronger demand for excess glucose, in order to produce lactate as main fermentation end product, than the wild type strain. It is known from earlier studies that a shift towards mixed acid product formation occurs when glucose becomes limited in lactococcal cultivation or when certain other sugars, such as maltose, are used as sole carbon sources [Lohmeier-Vogel, (1986); Cocaign-Bousquet, (1996); Sjöberg, (1995)]. This is due to a diminished flux through glycolysis and a lower $NADH/NAD^+$ ratio. It has further been explained that the bottleneck under such conditions most probably is at the level of sugar transport.

Glucose Uptake and Enzyme Activities

Measurements of glucose uptake in lactococcal cells cultivated under non-limiting glucose conditions were enabled using $^{14}C$-labelled glucose. The trend in glucose transport, using a range of glucose concentrations of 0.3125 mM to 200 mM, was shown to be saturating when higher glucose concentrations than approximately 20 mM was used in the assay for 19435 (FIG. 1). On the other hand, when TMB5003 was applied in the same assay the trend of glucose uptake did not show a saturating curve, although, for which reason is to us unknown, lower values of specific uptake rates were obtained. These results indicate that a regulatory function aimed at controlling the influx of sugar into lactococci is affected in the mutant cells. This may also be reflected upon when considering the more pronounced effect of shift towards mixed acid product formation for the mutant lactococci strain at glucose levels not considered to be limiting for the wild type lactococci (Table 1). There are evidences of two glucose transport systems in L. lactis, PTS and permease mediated, respectively [Thompson, (1985); Thompson, (1983)]. Due to the fact that glucose is transported by the mannose specific PTS in L. lactis it was tempting to check the growth rate of the lactococcal strains on this carbohydrate. Hence, both strains were shown to grow at the same specific growth rate as in their glucose cultures, respectively (data not shown). Despite the fact that many reports describe the regulatory role of PTS on the uptake of PTS- and non-PTS-sugars, via the glucose effect, there are not much information concerning regulation of uptake of glucose itself. The heat-stable protein (HPr) of the PTS and the HPr kinase are known to take part in the inducer expulsion and exclusion phenomena, and there are also suggestions of these to play a role in control of glucose uptake [Cocaign-Bousquet, (1996); Saier Jr., (1996)]. It is tempting to speculate that these proteins might be affected in TMB5003 and thus mediate the altered mode of glucose uptake in this strain. However, due to the fact that TMB5003 did also have an improved specific growth rate when cultivated on mannose, but not on trehalose, also suggested to be transported by PTS (Nilsson and Radstrom, (2001)), further speculations occur concerning the mannose specific components of the mannose/glucose uptake system to be affected in the mutant strain.

In L. lactis phosphofructokinase (PFK), pyruvate kinase (PK) and lactate dehydrogenase (LDH) are the key enzymes in the central pathway of energy production, the conversion of carbohydrates into lactic acid [Llanos, (1993)]. The genes encoding these enzymes are located together in an operon, denoted as the las-operon, on the chromosome. Recent results have been obtained concerning the role of PFK on glycolytic flux in L. lactis [Andersen, (2001)]. The conclusions were that glycolytic and lactate fluxes were decreased proportionally by a twofold reduction of PFK activity. Activities of the enzymes encoded by the las-operon were investigated in 19435 and TMB5003 cultivated at different dilution rates (Table 2). For mutant lactococci no difference in activities of PK and PFK could be detected in cell extracts from cultivations at the three different dilution rates. However, activities of LDH detected in TMB5003 cells collected at different growth rates differed markedly. LDH activity was higher in fast growing cells and it was showed to be twenty times higher in TMB5003 than in 19435 compared at the highest dilution rate for each strain respectively. These results are in consistence with recent findings of high LDH activities at high glycolytic rates for lactococci [Even, (2001)]. The markedly higher LDH activity in TMB5003 is most probably a response to the altered transport of glucose into the cells. Since the lactococci are provided with excess glucose and glycolytic flux is high, the mode of pyruvate conversion has to proceed accordingly due to the requirement of regeneration of $NAD^+$. This is performed by the reduction of pyruvate to lactate catalysed by LDH, which activity is therefore required to be kept high. In L. lactis it has been shown that in vivo glyceraldehyde phosphate dehydrogenase (GAPDH) activity limits the glycolytic flux on rapidly metabolizable sugars, due to the inhibition of a high $NADH/NAD^+$ ratio [Even, (1999)]. Therefore, we wanted to investigate if TMB5003 possessed an altered activity of GAPDH compared to wildtype lactococci. However, no difference in activities could be detected in the strains (Table 2).

The investigations of glucose uptake of the respective strain at controlled fermentation runs, at highest possible dilution rate with regard to each individual strains, were carried out. The results show that the new mutant TMB5003 has an unlimited uptake of glucose while a certain saturation of the uptake of glucose by the wildtype strain 19435 is noted. This is evident from FIG. 1, which shows specific uptake rates given as nmol/min/mg of cells added to the assay, versus the concentration of glucose given as mM added to the assay.

The concentrations of glucose were varied between 0 to 80 mM, and the specific uptake rate varied between 10 to 150 nmol/min/mg cells added, with regard to the wildtype strain, and between 5 to 55 nmol/min/mg cells added with regard to the new mutant.

The fermentation rates when grown on a glucose medium were compared as well, as evident from FIG. 2. The new mutant TMB5003 ferments glucose at the double rate compared to the wildtype strain. FIG. 2 shows both growth on glucose (optical density graph, OD-curve), and glucose consumption of the wildtype strain 19435, and TMB5003, respectively.

In Table 1 below the results of studied lactate formation is given.

TABLE 1

|  | Dilution rate (D) | | | | | |
| --- | --- | --- | --- | --- | --- | --- |
|  | L. lactis ATCC 19435 | | | L. lactis TMB5003 | | |
|  | 0.1 | 0.2 | 0.4 | 0.1 | 0.4 | 0.8 |
| $Y_{LA/tot}$ | 0.7 | 0.6 | 0.8 | 0.1 | 0.3 | 0.8 |
| $Q_s$ (g/g/h) | 0.4 | 0.6 | 2.0 | 0.03 | 0.5 | 3.1 |
| $Q_v$ (g/l/h) | 0.3 | 0.6 | 1.6 | 0.04 | 0.6 | 3.4 |

$Y_{LA/tot}$ stands for yield of lactic acid in relation to total production of fermentation products.
$Q_s$ is specific productivity, i.e., grams per gram of substrate.
$Q_v$ is volumetric productivity, i.e., grams per liter of broth per hour.

Furthermore the production of different enzymes present was analysed. The enzymes of interest are hereby the LDH, phosphofructokinase (PFK), the pyruvate kinase (PK) and the glyceraldehyde phosphate dehydrogenase (GAPDH). Comparisons are made at the highest D of the respective strain. The results are given in Table 2 below.

TABLE 2

| Enzyme | L. lactis 19435 D = 0.4 U/mg | L. lactis TMB5003 D = 0.8 U/mg |
|---|---|---|
| Lactate dehydrogenase (LDH) | 0.35 | 7.5 |
| Phosphofructokinase (PFK) | 0.5 | 0.5 |
| Pyruvate kinase (PK) | 0.15 | 0.1 |
| Glyceraldehydephosphate dehydrogenase (GAPDH) | 0.03 | 0.02 |

As evident from Table 2 above the production and activation of LDH is outstanding as compared to the wildtype, as it is at least 20 times that of the wildtype, which means that the present new strain has a higher capacity of producing lactate into the growth medium. With regard to the other enzymes analysed there are no differences to be seen between the two strains.

The L-lactate produced and recovered can be used to adjust pH in food, as a taste enhancer in food, as well as a preservative of food, whereby the preservative effect is due to a lowering of pH, as well as due to the weak acid itself, which prevents growth of a number of micro-organisms in food and feedstuff. Accumulation of anions intracellularly or uncoupling of ATP-syntase is thereby the most probable mechanisms of growth inhibition.

Further, the lactate can be used for the treatment of paper and metallic surfaces.

The lactate can be used for a polymerisation into polylactic acid, PLA, which is a biodegradable polymer. Further, the lactate can be used in the production of other compounds, such as propylene glycol, propylene oxide, acetaldehyde, ethanol, acrylates, and acrylic esters.

PLA as such can be applied in medical applications in the form of implants and sutures, production of items used for controlled release of drugs, and pesticides. The polylactate can be used in the manufacture of package materials, as well as biodegradable disposable items.

The present strain can be grown in different media, such as complex media based on tryptone, yeast extracts, and casamino acids. Glucose can be added as an external carbon source. However, complex media are not preferred, as the amount of sugar (glucose) which results in lactate formation shall be controlled. In tryptone and yeast extracts there will be unknown components present which may make this difficult. A semi-defined media, such as SD3 and an addition of glucose up to 5 g/l can be used.

The semi-defined medium (E. W. J van Niel and B. Hahn-Hagerdal (1999), "Nutritient requirements of lactococci in defined growth media", Applied Microbial Biotechnology 52:617-627) used for cultivating the present strain TMB5003 in the investigations made is composed of

| SD3 medium (per liter) | |
|---|---|
| Casamino acids | 10 g |
| $K_2HPO_4$ | 2.5 g |
| $KH_2PO_4$ | 2.5 g |
| $MgSO_4 \cdot 7H_2O$ | 0.5 g |
| Yeast nitrogen base (except casamino acids (Difco)) | 5 g |
| Asparagine | 0.4 g |
| Reduced glutathione | 10 mg |
| Uracil | 60 mg |
| Adenine | 30 mg |

-continued

| SD3 medium (per liter) | |
|---|---|
| Guanine | 30 mg |
| Vitamin solution | 10 ml |
| Trace element solution | 1 ml |
| Glucose | 5 g |

| Vitamin solution (per liter) | |
|---|---|
| D-biotin | 10 mg |
| Pyridoxal-HCl | 206 mg |
| Folic acid | 100 mg |
| Riboflavin | 100 mg |
| Niacinamide | 100 mg |
| Thiamine-HCl | 100 mg |
| Ca-D-panthotenate | 95 mg |
| p-Aminobenzoic acid | 10 mg |

| Trace element solution (per liter) | |
|---|---|
| $Ca_2$-EDTA | 15 g |
| $ZnSO_4 \cdot 7H_2O$ | 4.5 g |
| $MnCl_2 \cdot 2H_2O$ | 1 g |
| $CoCl_2 \cdot 6H_2O$ | 0.3 g |
| $CuSO_4 \cdot 5H_2O$ | 0.3 g |
| $Na_2MoO_4 \cdot H_2O$ | 0.4 g |
| $CaCl_2 \cdot 2H_2O$ | 4.5 g |
| $FeSO_4 \cdot 7H_2O$ | 3 g |
| $H_3BO_3$ | 1 g |
| KI | 0.1 g |

The solutions of vitamins, trace elements, nucleic acid bases, yeast nitrogen base, asparagine and reduced glutathione were filter sterilised and added to the medium aseptically. The other components were autoclaved separately. At selection of TMB5003 2 μg of erythromycin /ml medium is added.

It is preferred that the present mutant TMB5003 is grown at high dilution rate, i.e., with a complete addition of glucose, and absolutely no restricted addition thereof to obtain and maintain a maximal lactate production. Thus a dilution rate of at least $0.5h^{-1}$, preferably at least $0.7h^{-1}$, and most preferably at least $0.8h^{-1}$ is used. At a restricted addition of glucose during growth the lactate production tends to drop to the benefit of formation of by-products such as other acids such as acetate (acetic acid) and formate (formic acid).

It is, so far, very probable that the limiting factor of the wildtype strain to produce lactate is the ability of the strain to transport glucose. The flux by means of the glucolysis is probably not limiting. The final pyruvate metabolism may be limiting. LDH is the enzyme which transforms pyruvate into lactate and this enzyme has turned out to have different temperature optima depending on which strain of lactococci that is used at the fermentation of glucose. pH, as well, may have an effect upon the activity of LDH. Furthermore, the redox balance influences the efficiency of the LDH. The presence of the co-factors $NAD^+$/NADH is the controlling factor.

The conditions for enhancing L-LDH activity are fermentation in a medium having a pH above 6, and a temperature of up to 30° C., at which conditions L-lactate is substantially the only isomer produced, while D-LDH is activated at pH 4-5, and 33.5 to 40° C. Thus the fermentation of the present mutant should be carried out at such conditions that enhance activity of L-LDH to enhance formation of L-lactate. Thus, the pH and temperature conditions for production of L-lactate are pH 6 to 7, preferably 6.0 to 6.5, and using a temperature of 25 to 30° C., preferably 27.5 to 30° C.

FIGURE LEGENDS

Figure 1A:
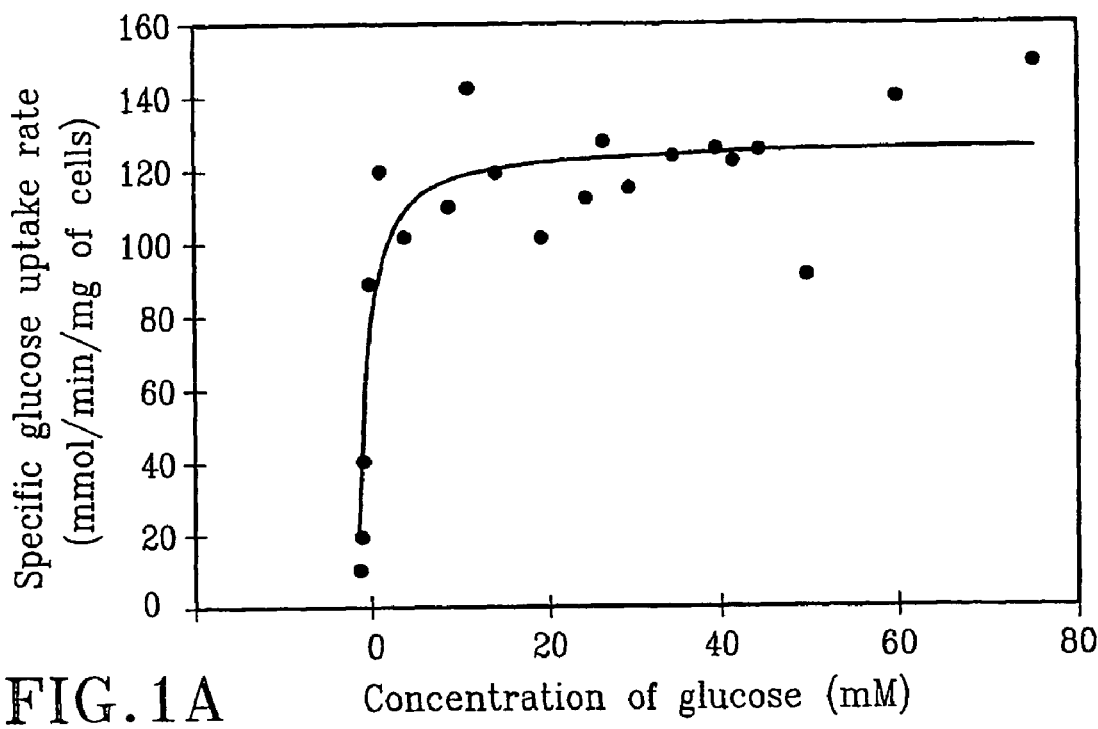
FIG. 1A shows the specific glucose uptake rate *Lactococcus* lactis spp. *lactis* 19435 cultivated at a dilution rate of 0.4 $h^{-1}$.
Figure 1B:
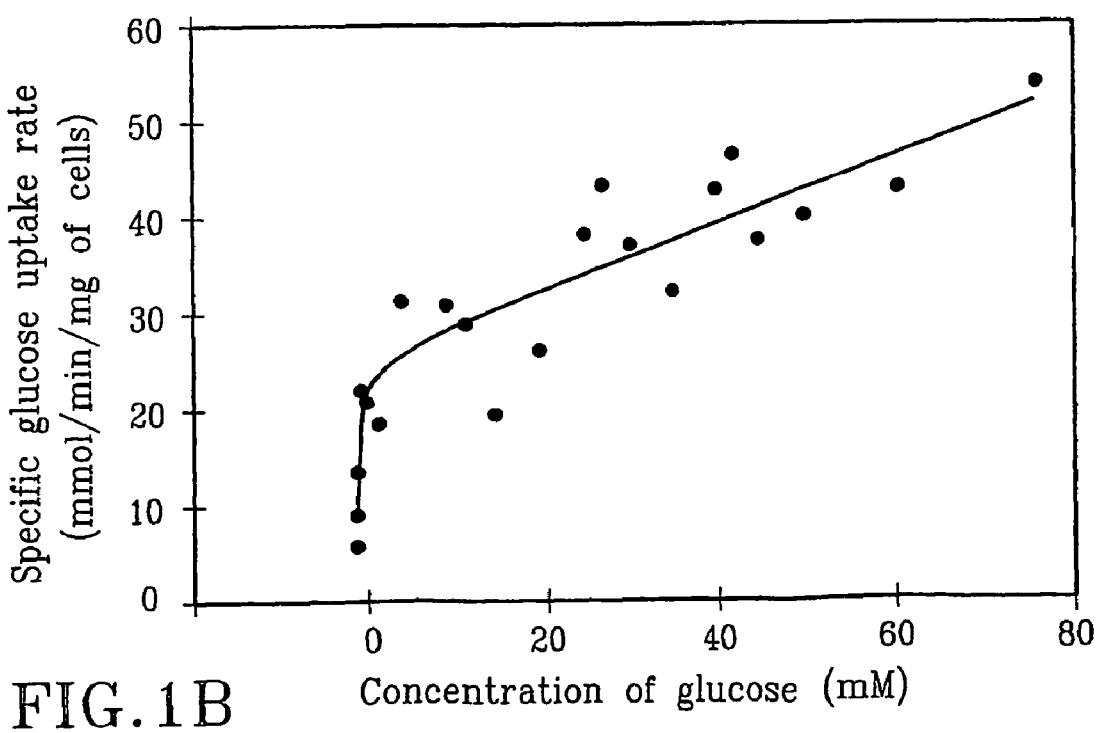
FIG. 1B shows the specific glucose uptake rate by *Lactococcus* lactis spp. *lactis* TMB5003 cultivated at a dilution rate of 0.8 $h^{-1}$.
Figure 2:
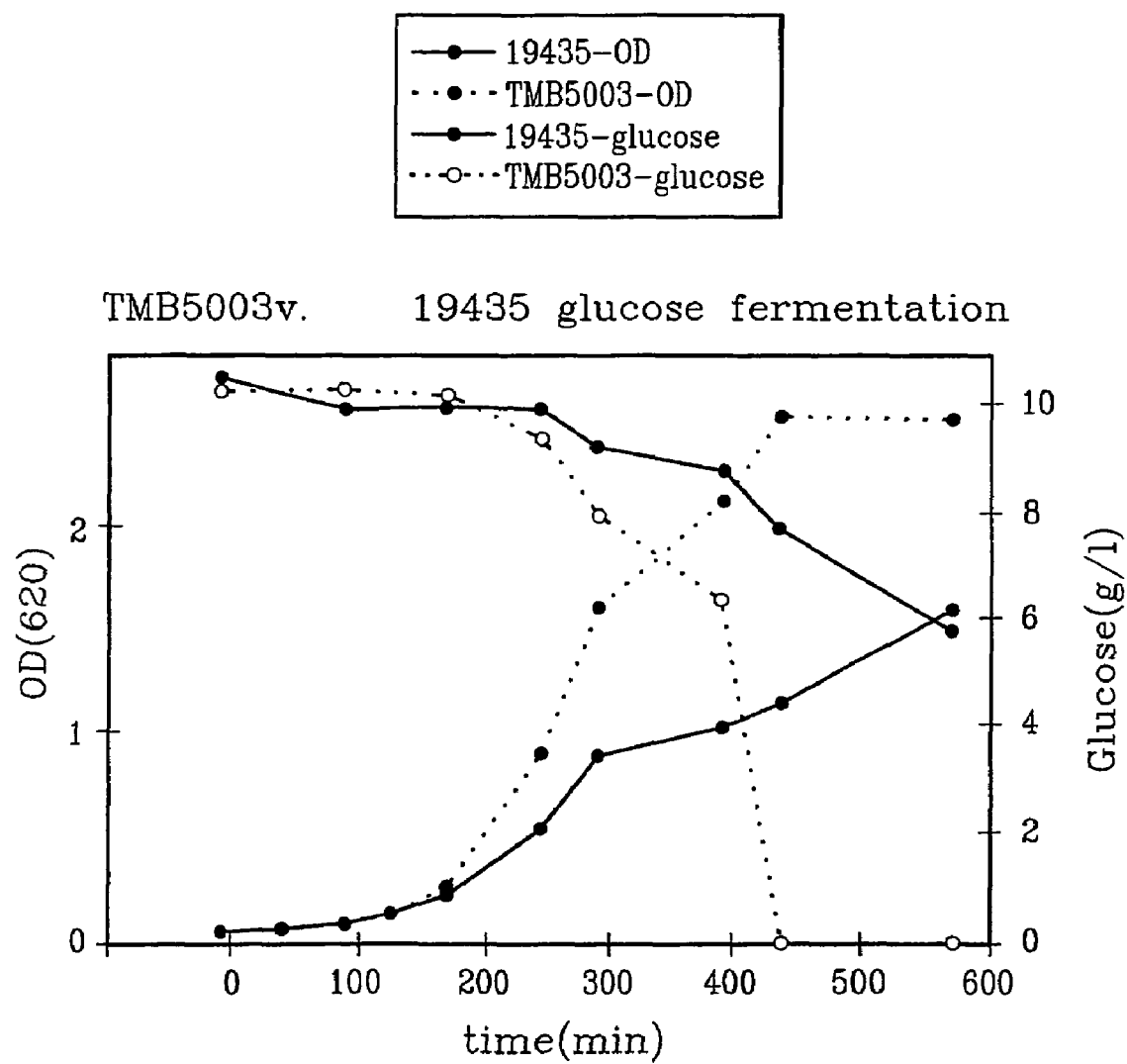
FIG. 2 shows the glucose consumption versus time, and the change of optical density (OD) versus time.

The invention claimed is:

1. An isolated mutant of *Lactococcus lactis* spp. *lactis*, which, during continuous fermentation, using glucose as the sole carbon source under non-limiting conditions,
    produces lactate at high volumetric productivity, which is at least twice that of the *Lactococcus lactis* spp. *lactis* 19435, and
    produces lactate at specific productivity, which is at least 1.5 times that of the *Lactococcus lactis* spp. *lactis* 19435, and
    produces high amounts of lactate dehydrogenase, which is at least twenty times that of the *Lactococcus lactis* spp. *lactis* 19435.

2. A method for the production of lactate on a glucose containing medium, wherein an inoculum of *Lactococcus lactis* spp. *lactis* TMB5003 is grown on a medium comprising glucose as carbon source, and the lactate thus formed is isolated.

3. A method according to claim 2, wherein the growth is continuous at a dilution rate of at least 0.5 $h^1$.

4. A method according to claim 3, wherein the growth is continuous at a dilution rate of at least 0.7 $h^1$.

5. A method according to claim 4, wherein the growth is continuous at a dilution rate of at least 0.8 $h^1$.

6. A method according to claim 2, wherein the growth is carried out at unrestricted feed of glucose.

7. A method according to claim 2, wherein the growth is carried out at a pH of above 6.

8. A method according to claim 2, wherein the growth is carried out at a temperature of between 25 and 30 C.

9. The method according to claim 7, wherein the pH is 6-7.

10. The method according to claim 8, wherein the temperature is 27.7 to 30 C.

* * * * *

UNITED STATES PATENT AND TRADEMARK OFFICE
CERTIFICATE OF CORRECTION

PATENT NO. : 7,537,925 B2
APPLICATION NO. : 11/336523
DATED : May 26, 2009
INVENTOR(S) : Andersson et al.

Page 1 of 1

It is certified that error appears in the above-identified patent and that said Letters Patent is hereby corrected as shown below:

Title Page, line 27, Item (30) should read:

-- (30) Foreign Application Priority Data

October 3, 2001 SE ..........................0103294-4 --

Signed and Sealed this

Fourth Day of August, 2009

JOHN DOLL
*Acting Director of the United States Patent and Trademark Office*